United States Patent [19]

Krebber et al.

[11] Patent Number: 5,514,548
[45] Date of Patent: May 7, 1996

[54] METHOD FOR IN VIVO SELECTION OF LIGAND-BINDING PROTEINS

[75] Inventors: Klaus Krebber, Zurich, Switzerland; Simon Moroney, Munich, Germany; Andreas Plückthun, Zurich, Switzerland; Christian Schneider, Bergisch-Gladbach, Germany

[73] Assignee: Morphosys Gesellschaft fur Proteinoptimerung mbH, Munich, Germany

[21] Appl. No.: 197,770

[22] Filed: Feb. 17, 1994

[30] Foreign Application Priority Data

Feb. 17, 1993 [EP] European Pat. Off. .............. 93102484

[51] Int. Cl.$^6$ ............................ C12Q 1/68; C12N 15/64; C12N 15/70
[52] U.S. Cl. ...................... 435/6; 435/172.3; 435/320.1; 530/350
[58] Field of Search .................... 435/6, 320.1, 172.3; 530/300, 350

[56] References Cited

FOREIGN PATENT DOCUMENTS

WO92/01047  1/1992  WIPO .......................... C12N 15/00

OTHER PUBLICATIONS

S. Bass et al., "Hormone Phage: An Enrichment Method for Variant Proteins with Altered Binding Properties", *Proteins*, 8, pp. 309–314 (1990).
M. Better et al., "*Escherichia coli* Secretion of an Active Chimeric Antibody Fragment", *Science*, 240, pp. 1041–1043 (1988).
R. Ebright et al., "Corrected Nucleotide Sequence of M13mp18 Gene III", *Gene*, 114, pp. 81–83 (1992).
B. Friguet et al., "Polypeptide–Antibody Binding Mechanism: Conformational Adaptation Investigated by Equilibrium and Kinetic Analysis", *Res. Immunol.*, 140, pp. 355–376 (1989).
L. J. Garrard and E. A. Zhukovsky, "Antibody Expression in Bacteriophage Systems: The Future of Monoclonal Antibodies?", *Current Opinion in Biotechnology*, 3, App. 474–480 (1992).
L. J. Garrard et al., "F$_{ab}$ Assembly and Enrichment in a Monovalent Phage Display System", *Bio/Technology*, 9, pp. 1373–1377 (1991).
L. Ge et al., "Expressing Antibodides in *Eschericia coli*" in *Antibody Engineering: A Practical Approach (IRL Press, C. Borrebaeck et al., eds., in press)*, pp. 1–49.
H. Gram et al., "In vitro Selection and Affinity Maturation of Antibodies From A Naive Combinatorial Immunoglobulin Library", *Proc. Nat. Acad. Sci., USA*, 89, pp. 3576–3580 (1992).
E. Hochuli et al., "Genetic Approach to Facilitate Purification of Recombinant Proteins with a Novel Metal Chelate Adsorbent", *Bio/Technology*, 6, pp. 1321–1325 (1988).
W. D. Huse et al., "Generation of a Large Combinatorial Library of the Immunoglobulin Repertoire in Phage Lambda", *Science*, 246, pp. 1275–1281 (1989).

P. T. Jones et al., "Replacing the Complementarity–Determining Regions in a Human Antibody with Those from a Mouse", *Nature*, 321, pp. 522–525 (1986).
D. W. Leung et al., "A Method For Random Mutagenesis of a Defined DNA Segment Using a Modified Polymerase Chain Reaction", *Technique*, 1, pp. 11–15 (1989).
J. D. Marks et al., "By–Passing Immunization: Building High Affinity Human Antibodies by Chain Shuffling", *Bio/Technology*, 10, pp. 779–783 (1992).
J. McCafferty et al., "Phage Antibodies: Filamentous Phage Displaying Antibody Variable Domains", *Nature*, 348, pp. 552–554 (1990).
G. E. Means and Robert E. Fenney, "Chemical Modifications of Proteins: History and Applications", *Bioconjugate Chemistry*, 1, pp. 2–12 (1990).
S. L. Morrison "In Vitro Antibodies: Strategies for Production and Application", *Annu. Rev. Immunol.*, 10, 239–265 (1992).
K. F. Nelson et al., "Filamentous Phage DNA Cloning Vectors: A Noninfective Mutant with a Nonpolar Deletion in Gene III", *Virology*, 108. pp. 338–350 (1981).
A. Plückthun and A. Skerra, "Expression of Functional Antibody F$_v$ and F$_{ab}$ Fragments in *Escherichia coli*", *Methods in Enzymology*, 178, pp. 497–515 (1989).
A. Plückthun, "Mono–and Bivalent Antibody Fragments Produced in *Escherichia coli*: Engineering, Folding and Antigen Binding", *Immunol. Rev.*, 130, pp. 151–188 (1992).
B. Singer and J. T. Kúsmierek, "Chemical Mutagensis", *Ann. Rev. Biochem*, 52, pp. 655–693 (1982).
A. Skerra and A. Plückthun "Assembly of a Functional Immunoglobulin F$_v$ Fragment in *Escherichia coli*", *Science*, 240, pp. 1038–1041 (1988).
A. Skerra and A. Plückthun, "Secretion and In Vivo Folding of the F$_{ab}$ Fragment of the Antibody McPC603 in *Escherichia coli*: Influence of Disulphides and cis–Prolines", *Protein Engineering*, 4(8), pp. 971–979 (1991).
A. Skerra et al., "The Functional Expression of Antibody F$_v$ Fragments in *Escherichia coli*: Improved Vectors and a Generally Applicable Purification Technique", *Bio/Technology*, 9, pp. 273–278 (1991).

(List continued on next page.)

*Primary Examiner*—Mindy Fleisher
*Assistant Examiner*—James Ketter
*Attorney, Agent, or Firm*—Fish & Neave; James F. Haley, Jr.

[57] ABSTRACT

The application discloses a method, and kit, which enables the selection of proteins or other oligo- or polypeptides (collectively, ligand binding proteins, LBPs) which bind with high affinity to a target ligand or receptor. The method relies on the display of the LBP of interest on the surface of replicable genetic packages (RGPs) which are modified so as to be non-infective. Infectivity is restored to those RGPs displaying LBPs with high affinity for a target ligand or receptor by an infectivity mediating complex. The infectivity mediating complex comprises the ligand or receptor covalently linked to a polypeptide which brings about interaction between the RGP and a host cell. It is envisaged that the LBP of interest will belong to a genetically diverse collection of similar substances. The method therefore allows selection of substances with high affinity for target, from within a large collection of variants.

27 Claims, 1 Drawing Sheet

OTHER PUBLICATIONS

G. P. Smith, "Surface Presentation of Protein Epitopes Using Bacteriophage Expression Systems", *Current Opinion in Biotechnology,* 2, pp. 668–673 (1991).

C. J. Suckling et al., "Catalytic Antibodies: A New Window on Protein Chemistry", Ciba Foundation Symposium 159 (John Wiley & Sons Ltd. 1991) pp. 201–210.

J. Travis and G. S. Salvesen, "Human Plasma Proteinase Inhibitors", *Ann. Rev. Biochem.,* 52, pp. 655–709.

METHOD FOR IN VIVO SELECTION OF LIGAND-BINDING PROTEINS

FIELD OF THE INVENTION

The present invention relates to a method for the selection of proteins or other oligo- or polypeptides which bind with high affinity to a target ligand or receptor. The invention relates in particular, but not exclusively, to a system which can be used to select among a large population of variants for antibodies having high affinity for a target antigen.

BACKGROUND OF THE INVENTION

The advent of methods for the production of functional antibody fragments in recombinant bacteria (1, 2) has opened the way to genetic manipulation of antibody genes. As a result of this development, genetic engineering is increasingly being used to generate antibodies for particular applications. Examples of this methodology are antibody chimerization (3) and humanization (4). These processes produce antibodies better suited to human therapeutic applications than their typically murine progenitors, by altering parts of the antibody molecule which are recognized as foreign by the human immune system.

Although genetic engineering can be used to make almost any desired change in an antibody structure, it cannot as yet provide solutions to some of the most pressing problems in antibody generation. For example, a common goal is affinity maturation, the optimization of antibody-antigen interaction. In most cases, the three dimensional structure of the antigen is unknown, which makes rational design of the antibody binding site so as to increase affinity almost impossible. Therefore, the ability to alter antibody genes at will does not necessarily help in affinity maturation. Similarly, genetic engineering does not allow generation of human antibodies, which are desirable for therapeutic purposes, but which cannot, for ethical reasons, be generated by immunizing volunteers. Problems such as these demand a new approach to antibody generation.

A promising approach relies on searching for antibodies having the desired properties within a large collection (library) of variants. Methods for generating such antibody libraries, and searching through them, have recently been developed (see, for example, (5) and (6) and references therein). This approach is attractive because:

It relies on strong binding of the antibody to a target antigen, and is therefore well-suited to affinity maturation.

Antibodies which are not available by immunization (for example, human antibodies) can be accessed.

Currently, the most efficient approach to antibody affinity maturation uses the following technique. Antibody genes from a suitable source (such as, for example, human peripheral blood lymphocytes, or human bone marrow) are cloned in bacteriophage in such a way that antibody fragments are displayed as fusion proteins on the surface of the phage (7). The phages are produced from bacterial host cells, generating a "phage library" in which every phage contains the genetic information for the antibody variant displayed on its surface. This library can be searched for antibodies which bind to the target antigen.

Locating the highest affinity antibodies within such a library is typically performed by screening: a physical process in which high affinity antibodies are separated from others through their ability to bind to immobilized antigen. The screening process involves immobilizing the target substance on a solid support and performing affinity chromatography or "panning" (8) of the phage library. Those antibodies with high affinity for the immobilized antigen are thereby enriched, and their numbers can be increased by propagation of the specifically eluted phage in bacterial host cells.

Initial results show that antibodies with moderate target affinity can be generated in this way. Higher affinities can, in principle, be obtained by performing random mutagenesis on the antibodies isolated in the first screening, and repeating the process one or more times. For example, random mutagenesis of antibody-encoding genes (9), and random shuffling of the genes encoding the component chains of the antibody (10) have been used to generate new antibodies with increased affinity or altered specificity, which have been located within the mutant libraries by screening.

Although a useful tool for antibody affinity maturation, library screening suffers from two main disadvantages. First, the probability of finding a high affinity antibody is related to the size of the library. Due to technical limitations associated with the efficiency with which bacterial cells can be transformed by plasmid DNA, libraries rarely contain more than $10^8$ members. This is not large enough to contain high affinity antibodies routinely. Second, phage isolated by screening must be used to re-infect bacteria if the system is to be run over multiple rounds. The overall process is therefore discontinuous, and as the physical separation and re-infection steps are time-consuming and labour intensive, the method is not well suited to multiple rounds of screening.

These disadvantages are overcome by the present invention, which provides for an artificial method of antibody optimization based on biological selection rather than screening. The invention provides for a library of antibodies, or other ligand or receptor binding oligo- or polypeptides, to be displayed on the surface of phage. The invention requires that the phage are rendered non-infectious by modification of a minor coat protein required for infectivity. Phage which display oligo- or polypeptides with high affinity for a target ligand or receptor are selected from a library by conferring on them the ability to be propagated. The invention provides that phage displaying oligo- or polypeptides with lower target affinity are not propagated. Infectivity is conferred by a substance comprising the target ligand or receptor linked to a portion of the phage coat protein which is required for infectivity.

The main advantage over existing methods offered by the present invention is that it can be carried out in a continuous fashion. In this regard, it mimics the system of clonal selection used by the immune system in antibody optimization. The present invention provides a system which is well-suited to affinity maturation of antibodies in multiple rounds of mutation and selection. Even at a single step, the present invention provides an enormous simplification over existing methods since it provides for propagation of only binding variants, thus obviating the requirement for any chromatography or "panning" step. Extremely large libraries can, in principle, be screened. Furthermore, single binding events are detected, giving the method which is the subject of the present invention a very high sensitivity. Finally, the invention is not restricted to antibody selection; it applies equally to any oligo- or polypeptide which interacts with a target ligand or receptor.

DETAILED DESCRIPTION OF THE INVENTION

Figure 1:
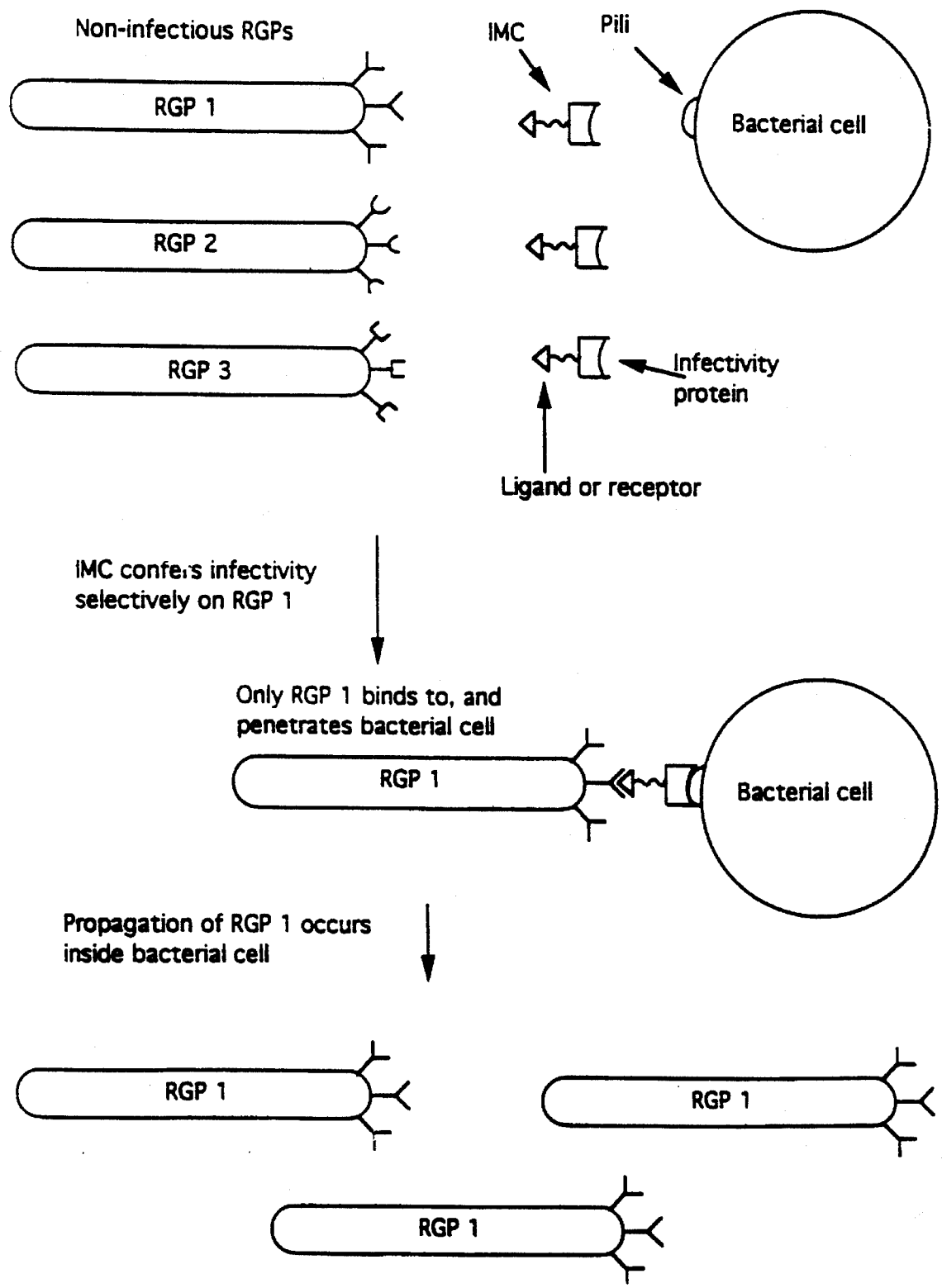

The present invention allows for the selection, from a library of specially modified phage displaying on their surface ligand binding proteins, of those which display ligand binding proteins which bind most tightly to a target ligand or receptor. The invention uses several components, which are described in more detail below.

Accordingly, the present invention relates to a method for selecting a gene by artificially conferring on it a preferential ability to be replicated, by using an infectious replicable genetic package (RGP) to couple the replicability of the gene to the interaction between the peptide or protein encoded by the gene and a particular target ligand or receptor. In this context, the term infectious replicable genetic package refers to an entity, such as a virus, or bacteriophage which can be replicated following infection of a suitable host cell. For example, the RGP may be one of the class of viruses known as bacteriophage, which infect bacterial cells. The term target ligand refers to any substance which is able to interact with the peptide or protein encoded by the gene to be selected.

In a further embodiment, the present invention relates to a method for selecting genes encoding ligand or receptor binding peptides or proteins (LBPs). In this context, the term LBP refers to any oligo- or polypeptide, or protein which is able to bind, to a greater or lesser extent, a target ligand or receptor. Particularly preferred is a method comprising the following steps (see Figure):

First, an infectious RGP is modified so as to remove its ability to infect a host cell, such modification being so as to allow infectivity to be restored as described below. The resulting RGP is thus non-infectious. For example, in the case where the RGP is a bactenophage, this is most readily achieved by modifying, so as to render defective, all copies of the coat protein which is essential in enabling the phage to infect a bacterial host cell.

Second, a set of DNA sequences encoding a genetically diverse collection of LBPs is inserted into the genome of the non-infectious RGP, using well-established techniques, in such a way that the LBPs are displayed on its surface. This may, for example, include the use of an expression phagemid and a separate helper virus or phage. By way of example, the LBP may be an antibody single chain Fv fragment. In this case, the target ligand is an antigen to which the fragment should bind. The LBPs may be heterologous, i.e. belong to a single family of substances, such as the antibodies, but possess different amino add sequences, as defined by the sequences of the DNA which encodes them. Typically, the LBPs, and the DNA sequences which encode them constitute a large collection or library of related, but genetically diverse substances.

Third, the genetic material is expressed in a recombinant host organism, thereby producing non-infectious RGPs displaying LBPs on their surface. In the case where the RGP is a bacteriophage, display of the LBPs can be achieved using existing protocols. For example, single chain Fv (scFv) or Fab antibody fragments can be displayed as fusions with either the gene HI or gene VIII protein of the male-specific bacterophages fd, f1, or M13 as disclosed by Winter et al. (11).

Fourth, host cells, non-infectious RGPs, and a substance referred to as an infectivity mediating complex (IMC) are combined. In this context, the IMC comprises a first portion which selectively interacts with one or more LBPs, and a second portion which confers on the corresponding non-infectious RGP the ability to infect host cells. For example, it has been shown that the infectivity of the filamentous bacteriophage fd-tet can be banished by removing 169 amino acids from the N-terminal portion of the gene III protein (12). This polypeptide is referred to hereafter as the infectivity polypeptide. An IMC may then consist of this infectivity polypeptide covalently linked to a target ligand or receptor. The complex may comprise at least two domains if the ligand is peptidic. Alternatively, the infectivity polypeptide may be covalently joined to the ligand or receptor using any suitable chemical cross-linking procedure (13).

Fifth, the host cells are propagated in liquid culture under conditions which allow equilibrium to be established between the LBPs displayed on the surface of the RGPs and the IMC. Those RGPs which become tightly associated with the IMC by interaction between a displayed LBP and the ligand thereby acquire infectivity. Within the library, of LBPs there will be a range of binding affinities for the ligand portion of the IMC. The system can be tuned to select for LBPs having a desired affinity constant by adjusting the concentration of the IMC in the culture medium. At high LMC concentrations, RGPs displaying LBPs with only moderate affinity for the target are infectious. As the concentration of the IMC is lowered, infectivity becomes restricted to those RGPs presenting LBPs with higher target affinity.

Only those RGPs which infect host cells can be replicated. These RGPs are secreted by the host cell, and are able to enter the cycle again. The medium becomes enriched in RGPs which display ligand-binding proteins with high affinity for the target ligand. Under suitable conditions, the system selects for LBPs which bind the ligand most strongly.

In a further step, the gene(s) encoding the LBP(s) displayed on the surface of the RGP(s) may be isolated. This is achieved by standard methods, for example, by PCR of the RGP genome using appropriate primers. The gene(s) thus isolated may be modified in any desired way, re-inserted into the RGP genome, and re-subjected to the selection process.

In a preferred embodiment of the present invention, the RGP described above is a filamentous phage (14). Filamentous phage offer the advantage in the present system that methods for the display of proteins on their surface have been developed (14). Particularly preferred are the filamentous phages of class I (such as fd, M13, f1, If1, Ike, ZJ/2, or Ff), and class II (such as Xf, Pf1, or Pf3).

In a preferred embodiment, the set of DNA sequences encoding a genetically diverse collection of LBPs replaces part of a gene encoding a surface protein, which is essential for binding to, and infection of, a host cell. This partial replacement must not compromise assembly of the phage particle. Particularly preferred is the case in which the surface protein gene described above is gene III of the filamentous bacteriophages. The set of DNA sequences may, for example, replace 507 nucleotides encoding 169 amino acids at the N-terminus of the gene III protein, which are essential for binding to F-pill of host cells.

In a preferred embodiment, the ligand-binding proteins should be immunoglobulins, or members of the immunoglobulin super-family, or any fragments thereof. In this context, the term immunoglobulins includes members of the classes IgA, IgD, IgE, IgG, and IgM. The term immunoglobulin super-family refers to all proteins which share certain structural characteristics with the immunoglobulins, including, for example, the T-cell receptor, or any of the molecules CD2, CD4, CD8 etc. Also included are fragments which can be generated from these molecules, such as Fv (a complex of the two variable regions of the molecule), single chain Fv (an Fv complex in which the component chains are joined by a linker molecule), Fab, or F(ab')2 (15).

In a preferred embodiment, the IMC is a single polypeptide chain comprising a first portion which, when closely associated with non-infectious RGP(s), confers on it/them the ability to infect host cells, and a second portion which binds, to a greater or lesser extent, to one or more LBPs. In this context, the second portion of the polypeptide may be a small peptide ligand, or it may be a receptor molecule. Also preferred is the case in which the IMC comprises a polypeptide which, when closely associated with non-infectious RGP(s), confers on it/them the ability to infect host cells, covalently linked to a non-peptidic ligand for one or more LBPs. In either case, the first portion of the IMC may, for example, comprise the N-terminal section of the gene III protein essential for infectivity. Alternatively, the IMC may incorporate any other protein which has the binding characteristics of the gene III protein. In this context, the term binding characteristics refers to the ability of a protein to interact with the F-pili of host bacterial cells. Specifically included are proteins encoded by a DNA sequence capable of hybridizing with gene III. In this context, the term hybridization refers preferentially to conventional hybridization conditions. Particularly preferred are stringent hybridization conditions.

In a preferred embodiment, the present invention also allows for subjecting the set of DNA sequences encoding a genetically diverse collection of LBPs to random or site-specific mutagenesis. In this context, random mutagenesis refers to the introduction of changes in the identity of the bases making up the set of DNA sequences, at random positions throughout its length. In contrast, the term site-specific mutagenesis refers to defined changes which are made at precise points in the sequence.

It is envisaged that mutagenesis may be performed by any one of a number of methods. For example, both random and site-specific mutagenesis may be effected by replicating the vector which contains the set of DNA sequences to be mutated using an oligonucleotide "cassette" according to well-established methods (16). Furthermore, random mutagenesis may be performed by any one of several additional methods. For example, mutator strains of bacteria can be used as host cells. Commonly used mutators are the mutD, mutH, mutL, routS, or mutt strains of *Escherichia coli*, which show deficient repair mechanisms, and therefore increased mutation rates.

Alternatively, random mutagenesis can be achieved by adding during host cell propagation a chemical mutagen, such as formaldehyde, hydroxylamine, methoxyamine, nitrous acid, bisulfite, hydrazme, N-ethyl-N-nitrosourea, or N-methyl-N'-nitro-N-nitrosoguanidine. Other mutagens, such as those listed in (17) may also be used.

Random mutagenesis may also be achieved by subjecting the set of DNA sequences to an error-prone polymerase chain reaction, as described for example in (18).

In a preferred embodiment, random mutagenesis is achieved by any combination of DNA oligonucleotide cassette-based mutagenesis, the use of mutator strains of bacteria, addition of a mutagen during the propagation of host cells, and subjecting said set of DNA sequences to an error-prone polymerase chain reaction.

In a further embodiment, the present invention relates to a kit for the selection of genes encoding LBPs comprising a specially designed vector, and an infectivity mediating complex precursor. The vector may be any one suitable for phage production, and must additionally contain a cloning site at which DNA can be readily inserted. In this context, the term cloning site refers to a region of the vector in which there is at least one restriction enzyme cleavage site, which can conveniently be used to insert a foreign DNA sequence. In a preferred embodiment, there are multiple restriction enzyme cleavage sites at this position. By way of example, the vector fd-tet (12) can, with appropriate modifications, be used according to the present invention.

The vector also displays the following features. It must be capable of being packaged as an infectious RGP, and contain a cloning site enabling the introduction of a set of DNA sequences encoding a genetically diverse collection of LBPs in such a way that the LBPs are displayed at the surface of the RGP when the vector is packaged.

Furthermore, the RGP must include a modification which removes its ability to infect a host cell, although the modification must be so as to allow infectivity to be restored by interaction between an LBP displayed on the surface of the RGP and the IMC.

The term LMC precursor refers to substance which can be used to prepare a complex comprising a ligand which is capable of binding to one or more LBPs, and a polypeptide which, when associated with an RGP, confers on it the ability to infect a host cell. For example, the IMC precursor may comprise a polypeptide which, when associated with an RGP, can confer on it the ability to infect a host cell, and which is, or can be, derivatized in such a way as to allow covalent attachment of a ligand to which one or more of LBPs is able to bind. In this context, derivatization refers to any chemical or biochemical modification which enables the formation of a covalent bond to a second entity. By way of example, any suitable cross-linking reagent can be used, such as N-succinimidyl 3-(2-pyridyldithio)propionate (SPDP), succinimidyl 4-(N-maleimidomethyl) cyclohexane-1-carboxylate (SMCC), m-maleimidobenzoyl-N-hydroxysuccinimide ester (MBS), N-succinimidyl (4-iodoacetyl) aminobenzoate (SIAB), or 1-ethyl-3-(3-dimethylaminopropyl) carbodiimide (EDC) (13).

Alternatively, the IMC precursor may comprise a vector incorporating three DNA sequences: a first DNA sequence encoding a portion of an infectivity polypeptide which, when associated with an RGP can confer on it the ability to infect a host cell; optionally, a second DNA sequence encoding a linker; and an adjacent cloning site which allows introduction of a third DNA sequence encoding a ligand to which one or more LBPs is able to bind.

In a preferred embodiment of the present invention, the specially designed vector can be packaged, and replicated as a filamentous bacteriophage. Particularly preferred are the filamentous bacteriophage of class I (such as M13, f1, If1, Ike, ZJ/2, or Ff) and class LI (such as Xf, Pf1, or Pf3).

In a preferred embodiment, the cloning site replaces part, or all of a gene encoding a surface protein which is required by the RGP for binding to, and infection of, a host cell. For example, this may be gene III of the filamentous bacteriophages and the cloning site may replace the N-terminal 169 amino adds of the gene.

Further embodiments of the present invention are characterised in the claims.

The figure shows:

Figure: Selective infection by one of three replicable genetic packages (RGPs), each of which displays a different type of ligand binding protein (LBP). The infectivity mediating complex (IMC) comprises an infectivity protein linked to a ligand or receptor to which the LBP displayed on the surface of RGP 1 binds. Selective interact/on between RGP 1 and the IMC results in infection of bacterial host cells by RGP 1, only. RGP 1 is propagated, RGPs 2 & 3 are not.

The example illustrates the invention

EXAMPLE 1

Selective infection of bacterial cells by phage displaying an anti-tryptophan synthase antibody, conferred by an infectivity mediating complex comprising a portion of tryptophan synthase, linked to a portion of gene III protein.

In the following description, all molecular biology experiments are performed according to standard protocols (16).

1. Construction of the infectivity mediating complex (IMC).

Long and short versions of gene III are amplified and cloned. In each case, PCR primer pairs are used which encode BspHI and BspEI restriction sites at the N-terminus and C-terminus respectively of the resulting cloned gene. Using the PCR primer pair AAT CAT GAA AAA ATT ATT ATT CGC AA (SEQ ID NO: 1) and AAA AGC TTA GTG ATG GTG ATG GTG ATG TCC GGA ACC GGA GCC (SEQ ID NO: 2), the N-terminal domain of the gene III protein of bacteriophage M13 is amplified and cloned from the vector M13mp18 (19). In this case, the first 256 amino acids of the gene III protein are encoded, including the long, glycine-rich linker, together with an 18 amino acid signal sequence at the N-terminal end. This is advantageous when separately folding domains are to be fused to the gene III protein. Alternatively, the PCR primer pair AAT CAT GAA AAA ATT ATT ATT CGC AA (SEQ ID NO: 3) and AAA AGC TTA TCC GGA CGG AGC ATT GAC AGG AGG TTG (SEQ ID NO: 4) is used to amplify and done the N-terminal region. In this case, only the first 203 amino adds of the gene III protein are encoded, and the long, glycine-rich region is not amplified. This is desirable to avoid excessive proteolysis, such as when it is necessary to make a fusion to a peptide. Each PCR product is cut with BspHI and BspEI.

An expression vector suitable for secreting proteins is prepared. In this case, a derivative of pASK40 is used (20), which contains a BspHI site overlapping the ATG start codon of the signal sequence, as well as a BspEI site. The two PCR products are cloned into the pASK40 derivative, giving the two vectors pCK101 and pCK102.

The two ligands tested in this case are fragments of *E. coli* tryptophan synthase (21). The C-terminal fragment of the β-subunit of tryptophan synthase is amplified from the *E. coil* genome by PCR using the primer pair AAT CAT GAC CGA TGA TGA AGC CC (SEQ ID NO: 5) and AAA AGC TTA GTG ATG GTG ATG GTG ATG GAT TTC CCC TCG TGC TTT (SEQ ID NO: 6). The complete β-subunit of tryptophan synthase is similarly amplified using the primer pair AAT CAT GAC AAC ATT ACT TAA CCC (SEQ ID NO: 7) and AAA AGC TTA GTG ATG GTG ATG GTG ATG GAT TTC CCC TCG TGC TTT (SEQ ID NO: 8). In each case, the primers also encode a C-terminal stretch of six histidines, which are included to facilitate purification of the fusion proteins by immobilised metal ion affinity chromatography (22). The two PCR products, and the two plasmids pCK101 and pCK102 are cut with BspEI and BglI. Ligation of each PCR product, vector, and the connecting linker oligonudeotide having the sequence CCGG ACC GGG (SEQ ID NO: 9)/CAT GCC CGGT (SEQ ID NO: 10), generates four product vectors.

The resulting four vectors pCK103, pCK104, pCK105, and pCK106 contain DNA encoding the fusion proteins:

pCK103: the first 169 and no acids of gene III connected to the whole of *E. coli* tryptophan synthase β-subunit, pCK104: the first 169 ammo adds of gene III connected to the C-terminal 71 amino adds of *E. coli* tryptophan synthase β-subunit, pCK105: the first 134 ammo acids of gene III connected to the whole of *E. coil* tryptophan synthase β-subunit, pCK106: the first 134 ammo adds of gene III connected to the C-terminal 71 amino acids of *E. coil* tryptophan synthase β-subunit.

The fusion proteins so produced are isolated from either of the *E. coli* strains W3110 or JM83 using Ni(II)-NTA chromatography according to standard methods (22).

2. Construction of the RGP

In this example, a phagemid is used. The tryptophan synthase proteins described in the previous section are recognised by the antibody 93-6 (21) which has been expressed as an Fab fragment using a standard periplasmic expression vector (23). In this vector, the light chain is fused to a shortened version of gene III, containing residues 214 to 424, following the work of Bass et al. (24). *E. coli* strain JM101 harbouring this plasmid is co-infected with the phage fKN-16 (12) which carries a 507 nucleotide deletion in gene III. Since this phage is non-infective, an extremely high phage titre needs to be used to obtain successful infection with this helper phage.

Next, bacteria are grown using standard methods (25) and phage are harvested as described. The phage comprise a mixture of packaged helper phage and packaged phagemid, each containing antibody-gene III fusion proteins in their coats. The two types of phage are easily discriminated, since the helper phage genome carries a gene encoding tetracyclin resistance, while the phagemid is ampicillin resistant. Phage are enriched by the usual PEG precipitation procedure (25).

3. Selective Infection

Phage and the IMC are mixed at about 1:1 stoichiometry and added to logarithmically growing *E. coil* JM101 cells. Both tetracyclin and ampicillin resistant colonies are obtained. Upon addition of tryptophan synthase, which interferes with binding of the β subunit to the fusion protein displayed on the surface of the phage, the number of colonies is drastically reduced. Furthermore, only few background dories are obtained if an irrelevant Fab fragment is added, for example, one directed against phosphorylcholine (26) expressed in the same phagemid vector.

The following example provides an improved demonstration of the method.

EXAMPLE 2

Application of the Method to Selection Between Two Antibody Fragments Recognizing Different Target Substances.

A. The Tryptophan Synthase β-Subunit/H936 Anti-Tryptophan Synthase System

(i) Construction of the Parent Cloning Vector pCK-XBD

The parent vector for all subsequent steps, pCK-XBD, was constructed from pASK29-L220 (27) by insertion of the self-complementary oligonucleotide CTA GAT AAG GAA AAA TCA TGA TTT TTC CTT AT (SEQ ID NO: 11) into the unique XbaI sit of the vector, thereby introducing a unique BspHI site, The start codon included in this BspHI site is ideally positioned six nucleotides downstream of the Shine-Dalgarno sequence, allowing for direct expression cloning of PCR products.

(ii) Construction of the Vectors pCK-IPM and pCK-IPS Encoding Infectivity Polypeptides Bearing a Hexa-histidine Tail PCR amplification of the N-terminal portion of gene III from the vector M13mp18 (19) was carried out using the primer pair AAT CAT GAA AAA ATT ATT ATT CGC AA (SEQ ID NO: 1) and AAA AGC TEA GTG ATG GTC ATG GTG ATG TCC GGA ACC CCA CCC (SEQ ID NO: 2). The resulting DNA was digested with BspHI and HindIII, purified, and ligated into the vector fragment of plasmid pCK-XBD which had been digested with the same enzymes. The resulting plasmid pCK-IPM expresses the polypeptide LPM which comprises the N-terminal 256 amino acids of the mature protein III linked to a hexa-histidine tail.

Similarly, the plasmid pCK-IPS was prepared by PCR amplification of gene III from the vector M13mp18 using the primer pair AAT CAT GAA AAA ATT ATT ATT CGC AA (SEQ ID NO: 3) and AAA AGC TTA GTG ATG GTG ATG GTG ATG TCC GGA CGG AGC ATT GAC AGG AGG TTG (SEQ ID NO: 12), digestion of the resulting DNA with BspHI and HindIII, purification of the fragment, and Ligation into the linearized vector derived from plasmid pCK-XBD by digestion with the same restriction enzymes. The resulting plasmid pCK-IPS expresses the polypeptide IPS, which comprises the N-terminal 217 amino acids of the mature protein III linked to the oligopeptide Pro-Ser-Gly-His-His-His-His-His-His.

(iii) Construction of Vectors Encoding Infectivity Polypeptide-Tryptophan Synthase β-Subunit Fusion Proteins.

The two target ligands of interest in this case are the C-terminal fragment of the β-subunit of tryptophan synthase from $E.\ coli$, and the complete β-subunit of tryptophan synthase (21). The encoding DNA was amplified by PCR using the primer pairs AAT CAT GAC CGA TGA TGA AGC CC (SEQ ID NO: 5) and AAA AGC TTA GTG ATG GTG ATG GTG ATG GAT TTC CCC TCG TGC TTT(SEQ ID NO: 6) (for amplifying the C-terminal fragment of the β-subunit—TSS) and AAT CAT GAC AAC ATT ACT AAA CCCC (SEQ ID NO: 7) and AAA AGC TTA GTG ATG GTG ATG GTG ATG GAT TTC CCC TCG TGC TTT(SEQ ID NO: 8) (for amplifying the entire subunit—TSB).

The TSS PCR product was digested with BspHI and HindIII. The plasmids pCK-IPM and pCK-IPS were digested with BspEI and HindIII and separately ligated with the TSS fragment and the connecting linker oligonucleotide pair CCG GAC CGG G (SEQ ID NO: 9) and CAT GCC CGG T (SEQ ID NO: 10) to generate the plasmids pCK-IPMTSS and pCK-IPSTSS respectively.

The TSB PCR product was digested with BspHI. The plasmids pCK-IPM and pCK-IPS were digested with HindIII and the single-stranded overhang was filled in, giving rise to blunt-ended, linearized vectors. These vectors were then digested with BspEI and the vector fragments were separately ligated with the TSB fragment and the co,meeting linker oligonucleotide pair CCG GAC CGG G (SEQ ID NO: 9) and CAT GCC CGG T (SEQ ID NO: 10) to generate the plasmids pCK-IPMTSB and pCK-IPSTSB respectively.

The infectivity-mediating complexes (IMCs) (the fusion proteins IPM-TSS, IPS-TSS, IPM-TSB, and IPS-TSB) were expressed in the $E.\ coli$ strain JM83, and purified by Ni(II)-NTA and anion exchange chromatography (22).

(iv) Preparation of Non-infectious RGPs Displaying a Single-Chain Antibody Recognising Tryptophan Synthase μ-Subunit and Carrying a Gene for Kanamycin Resistance The single-stranded DNA of phage fd was subjected to oligonucleotide-directed mutagenesis in order to remove a BspHI restriction site (using the oligonucleotide GAG GAC TAA AGA CTT ACG CAT GAG GAA GTT TCC (SEQ ID NO: 7), and to insert sites for the enzymes EcoRI (using TTG ACA GGA GGT TGA GGG AAT TCC AGG TCA GAC GAT T (SEQ ID NO: 14), BspHI (using CCA ATA ATA ATT TTT TCA TGA TGA AAA TCT CCA AAA AAA A (SEQ ID NO: 15), StuI and XhoI (using TTT AAT TGT ATC GGT CTC GAG AGG CCT TTA TCA GCT TGC (SEQ ID NO: 16), providing the vector fCK-VXZ.

To enable insertion of the gene for Kan resistance between gene VIII and gene III, a portion of the gene III promoter was duplicated in fCK-VXZ as follows. The product of PCR amplification of the phage vector fd with the primers GCG GGC CGC AGG CCT CGA GAA ATT CAC CTC G AA AGC AA (SEQ ID NO: 17) and CGA ATA ATA ATT TTT TCA TGA TGA AAA TCT CCA AAA AAA A (SEQ ID NO: 15) was digested with XhoI and BspHI, and ligated into the same sites in the phage fCK-VKZ, providing the phage fCK-I. The gone encoding kanamycin resistance was amplified from the plasmid pACYCI77 using the primers AGG CCT TAG AAA AAC TCA TCG AGC (SEQ ID NO: 18) and AGG CCT GTT ACA TTG CAC AAG ATA AAA ATA TAT CAT AAT GAA CAA TAA AAC TGT CT (SEQ ID NO: 19) and cloned directly into the StuI site of fCK-I, providing the phage-derived vector fCK-KAN.

A single-chain antibody Fv fragment (scFv) having the structure $V_L$-$V_H$ was cloned from the hybridoran H936 (21) and inserted into the vector pIG-6 (28). The scFv was amplified from the resulting plasmid by PCR using the primers AAA TCA TGA AAA AGA CAG CTA TCG CG (SEQ ID NO: 20) and GGT CAC GCT GCG CGT AAC C (SEQ ID NO: 21). The PCR product was digested with BspHI and EcoRI and cloned into the fCK-KAN vector fragment which had been digested with the same enzymes giving the phase vector fCK-H936. This phage vector encodes the H936 scFv as an N-terminal fusion of gene III. Phage particles (RGPs) displaying the scFv on their surface were prepared according to standard methods. The phage particles displayed on their surface single-chain antibody fragments that specifically recognized the β-subunit of tryptophan synthase, as demonstrated by ELISA.

B. The Benzoylampicillin/2H10 Anti-Benzoylampidllin System (i) Construction of the Vector pCK-IPMC Encodine an Infectivity Polypeptide Bearing a Pendant Cysteine Residue The plasmid pCK-IPM (see Example 2(ii) above) was digested with BspEI and HindIII, and the resulting vector fragment purified, and ligated with the oligonucleotide pair CCC GAT GCC CCC ATC ACC ATC ACC ATC ACT AAT ATT A (SEQ ID NO: 22) and AGC TTA ATA TTA GTG ATG GTG ATG GTG ATG GGG GCA T (SEQ ID NO: 2). The resulting vector, pCK-IPMC, differed from pCK-IPM in that it encoded the amino acids cysteine and proline between the last elycine and the six histidines at the C-terminus or the modified protein III expressed by pCK-IPM. The protein IPMC was obtained by expression of pCK-IFMC in the strain JM83, and purified by Ni(II)-NTA and anion exchange chromatography (22).

(ii) Construction of an infectivity-mediating complex by chemical coupling of Benzoyl ampicillin to an infectivity polypeptide bearing a pendant cysteine residue Ampicillin was coupled to the water-soluble cross-linker M-maleimidobenzoyl-N-hydroxysulphosuccinimide ester, and the resulting complex was conjugated to the pendant cysteine residue of the IPMC protein using standard methods. The resulting infectivity-mediating complex IPMC-BzAmp was freed of excess ampicillin-MBS by gel filtration chromatography.

(iii) Preparation of Non-Infectious RGPs Displaying a Single-Chain Antibody Recognising Benzoyl Ampicillin and Carrying a Gene for Kanamycin Resistance The single-chain antibody Fv fragment having the structure VL-VH of the hybridoma 2H10 (29) was cloned according to standard methods into the pIG-6 vector (28). This vector was digested with EcoRV and EcoRI, and the fragment was cloned into the phage vector fCK-H936 which had been digested with the same enzymes, resulting in replacement of the H936 scFv gene by the corresponding gene for 2H10. The resulting phage vector, fCK-2H10 enabled preparation of phage particles (RGPs) according to standard methods. The phage particles displayed on their surface single-chain antibody fragments that specifically recognized benzoyl ampicillin, as demonstrated by ELISA.

C. Specific Restoration of Infectivity of Non-Infectious Phage in the Presence of IMCs A 1:1 mixture of RGPs displaying the H936 and 2H10 scFvs was prepared and incubated with either IPM-TSS, IPS-TSS, IPM-TSB, IPS-TSB (see A(iii) above) or IPMC-BzAmp (see B(ii) above). After 4 h at 25° C. or 12 h at 4° C., the mixture was added to a suspension of logarithmically growing E. coli XLI-blue cells, which were starved by shaking for 1 h in 80 mM NaCl and 10 mM MgSO4 at 37° C. After incubation for 1 h at room temperature, the cells were plated on YT-agar containing 50 ug/mL of kanamycin.

The use of either IPMTSB, IPSTSB, IPMTSS, or IPSTSS fusion proteins as IMCs resulted in refection of the bacteria by fCK-H936. In contrast, when IPMC-BzAmp was used as IMC, fCK-2H10 clones were specifically formed.

In the complete absence of any IMCs or precursors thereof, the phage particles described in A(iv) and B(iii) above were demonstrated to give rise to substantially fewer colonies than were obtained in the presence of the IMCs as described above. The use of either IPMC, IPM, or IPS instead of any of the IMCs resulted in the same number of clones, showing that there is only a low background of non-specific infection events.

References

1. Skerra, A. & Plückthun, A. Science, 240, (1988), 1038.

2. Better, M., Chang, C. P., Robinson, R. R. & Horwitz, A. H. Science, 240, (1988), 1041.

3. Morrison, S. L. Ann. Rev. Immunol. 10, (1992), 239.

4. Jones, P. T., Dear, P. H., Foote, J., Neuberger, M. S. & Winter, G. Nature, 321, 1986) 522.

5. Huse, W. D., Lakshimi, S., Iverson, S. A., Kang, A. S., Alting-Mees, M., Burton, D. R., Benkovic, S. J. & Lerner, R. A. Science, 246, (1989) 275.

6. Garrard, L. J. & Zhukovsky, E. A. Current Opinion in Biotechnology, 3, (1992), 474–480.

7. McCafferty, J., Griffiths, A. D., Winter, G. & Chiswell, D. J. Nature, 348, (1990), 552.

8. Garrard, L. J., Yang, M., O'Connell, M. P., Kelley, R. F. & Henner, D. J. Bio/Technology 9, (1991), 1373.

9. Gram H., Marconi, L-A. Barbas, C. F., Collet, T. A., Lerner, R. A. & Kang, A. S. Proc. Nat. Acad. Sci., U.S.A., 89, (1992), 3576.

10. Marks, J. D., Griffiths, A. D., Malmqvist, M., Clackson, T. P., Bye, J. M. & Winter G. Bio/Technology 10, (1992), 779–783.

11. Patent application WO 92/01047.

12. Nelson, F. K., Friedman, S. M., & Smith G. P. Virology 108, (1981), 338.

13. Means, G. E., & Feeney, R. E. Bioconjugate Chemistry, 1, (1990), 2.

14. Smith, G. P. Current Opinion In Biotechnology, 2, (1991), 668.

15. Plückthun, A. Immunol. Rev. 130, (1992), 151.

16. "Molecular Cloning, A Laboratory Manual", Sambrook, J., Fritsch, E. F., & Maniatis, T. (eds), 2nd Ed., Cold Spring Harbor Laboratory Press, 1989.

17. Singer, B., & Kusmierek, J. T. Ann. Rev. Biochem. 52, (2982), 655.

18. Leung, D. W., Chen, E., & Goeddel. D. V. Technique 1, (1989), 11.

19. Ebright, R., Dong, Q., & Messing, J. Gene, 114, (1992), 81.

20. Skerra, A., Plückthun, A., & Pfitzinger, 1. Bio/Technology, 9, (1991), 273.

21. Friguet, B., Djavadi-Ohaniance, L., & Goldberg, M. E. Res. Immunol. 140, (1989), 355.

22. Hochuli, E., Bannwarth, W., Döbeli, H., Gentz, R., & Stüber, D. Bio/Technology, 6, (1988), 1322.

23. Plückthun, A., & Skerra, Methods in Enzymology, 178 (1989), 497.

24. Bass S., Greene, R., & Wells, J. A. Proteins, 8, (1990), 309.

25. "An Introduction to Recombinant DNA Techniques", Hackett, P. B., Fuchs, J. A., & Messing, J. W., (eds) Benjamin/Cummings, Menlo Park, 1984.

26. Skerra, A., & Plückthun, A. Science, 240, (1988), 1038.

27. Skerra, A., & Plückthun, A. Protein Engineering, 4, (1991), 971–979.

28. Ge, L., Knappik, A., Pack, P., Freund, C., & Plückthun, A. in "Antibody Engineering: A Practical Approach", IRL Press, C. Borrebaeck et al. (Eds), in press.

29. Suckling, C. J., Tedford, C. M., Proctor, G. R., Khalaf, A. I., Bence, L. M., & Stimson, W. H. in "Catalytic Antibodies", Ciba Foundation Symposium 159, John Wiley & Sons Ltd., 1991, pp. 201–208.

We claim:

1. A method for selecting a gene by artificially conferring on the gene a preferential ability to be replicated, comprising the steps of:

(a) rendering non-infectious a replicable genetic package (RGP) which is connected to the product of the gene; and (b) selectively restoring infectivity to the RGP by allowing the product of the gene to associate with an infectivity mediating complex (IMC);

wherein the IMC comprises a target ligand coupled to a substance which enables the RGP to infect a host cell and be replicated.

2. A method for selecting genes encoding ligand or receptor binding peptides or proteins (LBPs) comprising the following steps:

(a) modifying a replicable genetic package (RGP) to remove the RGP's ability to infect a host cell, such modification being so as to allow infectivity to be restored according to (b) through (d) below;

(b) inserting into the genome of the RGP a set of DNA sequences encoding a genetically diverse collection of LBPs;

(c) expressing the DNA sequence in a recombinant host cell such that the LBP is displayed at the RGP's surface;

(d) combining a number of non-infectious RGPs according to (a) and (b) above, host cells, and an infectivity mediating complex (IMC) in a medium, wherein the IMC selectively interacts with one or more of the LBPs, and restores to the RGPs displaying the LBPs their ability to infect the host cells;

(e) propagating host cells under conditions in which RGPs becoming associated with the IMC via LBPs displayed on their surface acquire a restored ability to infect the host cells and be replicated;

(f) isolating from the host cells RGPs carrying the gene or genes encoding the LBPs, and, optionally;

(g) using the RGP again in the same process from (c) above, an additional one or more times;

(h) isolating the genes from the RGP.

3. The method according to claim 2, wherein the replicable genetic package (RGP) is a filamentous bacteriophage.

4. The method according to claim 3, wherein the filamentous bacteriophage is selected from the group consisting of fd, M13, f1, If1, Ike, Zj/2, Ff, Xf, Pf1, and Pf3.

5. The method according to claim 2 wherein the replicable genetic package (RGP) is modified by replacing a part of a gene encoding a surface protein necessary for the RGP's binding to and infection of a host cell with a set of DNA sequences encoding a genetically diverse collection of ligand or receptor binding peptides or proteins (LBPs).

6. The method according to claim 5 wherein the gene is gene III of the filamentous bacteriophages.

7. The method according to any of claims 2–6, wherein the ligand or receptor binding peptides or proteins (LBPs)

are selected from the group consisting of immunoglobulins, members of the immunoglobulin super-family, and any fragments thereof.

8. The method according to any of claims 2–6, wherein the infectivity mediating complex (IMC) is a single polypeptide chain comprising:
    (a) a first domain which, when closely associated with a non-infectious replicable genetic package (RGP), restores the RGP's ability to infect host cells, and;
    (b) a second domain comprising a ligand for one or more ligand or receptor binding peptides or proteins (LBPs).

9. The method according to any of claims 2–6, wherein the infectivity mediating complex (IMC) comprises a polypeptide which, when closely associated with a non-infectious replicable genetic package (RGP), restores the RGP's ability to infect host cells, covalently linked to a non-peptidic ligand for one or more of the ligand or receptor binding peptides or proteins (LBPs).

10. The method according to claim 8 wherein the infectivity mediating complex (IMC) comprises, at least in part, the N-terminal 169 amino acids of a gene III protein of the filamentous bacteriophages, or is partially encoded by a DNA sequence that hybridizes with gene III and encodes a peptide having the binding characteristics of the gene III protein.

11. The method according to claim 9 wherein the infectivity mediating complex (IMC) comprises, at least in part, the N-terminal 169 amino acids of a gene III protein of the filamentous bacteriophages, or is partially encoded by a DNA sequence that hybridizes with gene III and encodes a peptide having the binding characteristics of the gene III protein.

12. The method according to any one of claims 2–6, additionally comprising the step of subjecting the set of DNA sequences encoding a genetically diverse collection of ligand or receptor binding peptides or proteins (LBPs) to random or site-specific mutagenesis.

13. The method according to claim 12 wherein the random or site-specific mutagenesis is achieved by DNA oligonucleotide cassette-based mutagenesis.

14. The method according to claim 12 wherein the random mutagenesis is achieved by using mutator strains of bacteria as host cells.

15. The method according to claim 14 wherein the mutator strains are selected from the group consisting of mutD, mutH, mutL, mutS, and mutt strains of *Escherichia coli*.

16. The method according to claim 12 wherein the random mutagenesis is achieved by adding a mutagen during the propagation of the host cells.

17. The method according to claim 16, wherein the mutagen is selected from the group consisting of formaldehyde, hydroxylamine, methoxyamine, nitrous acid, bisulfite, hydrazine, N-ethyl-N-nitrosourea, or N-methyl-N'-nitro-N-nitrosoguanidine, and any combination thereof.

18. The method according to claim 12 wherein the random mutagenesis is achieved by subjecting the set of DNA sequences to an error-prone polymerase chain reaction.

19. The method according to claim 12 wherein the random mutagenesis is achieved by any combination of DNA oligonucleotide cassette-based mutagenesis, the use of mutator strains of bacteria, addition of a mutagen during the propagation of host cells, and subjecting the set of DNA sequences to an error-prone polymerase chain reaction.

20. A kit for the selection of genes encoding ligand or receptor binding peptides or proteins (LBPs) comprising:
    (a) a vector capable of being packaged as an infectious replicable genetic package (RGP), having the following features:
        (1) a cloning site which enables introduction of a set of DNA sequences encoding a genetically diverse collection of LBPs in such a way that the LBPs are displayed at the surface of the RGP when the vector is packaged;
        (2) a modification which removes the RGP's ability to infect host cells, such modification being so as to allow infectivity to be restored by interaction between an LBP displayed on the surface of the RGP and a substance which can restore the RGP's ability to bind to and infect host cells; and either or both of:
    (b) a polypeptide which can be used in the preparation of an infectivity mediating complex (IMC) and which comprises a portion of a protein which, when associated with the RGP, can restore its ability to infect a host cell, and which is able to form a covalent attachment of a ligand to which one or more LBPs is able to bind; and;
    (c) a vector having the following features:
        (1) a first stretch of DNA encoding a portion of an infectivity polypeptide which, when associated with the RGP, can restore its ability to infect a host cell,
        (2) a second stretch of DNA encoding a linker,
        (3) a third stretch of DNA comprising a cloning site which allows introduction of one or more DNA sequence(s) encoding (a) ligand(s) or receptor(s) to which one or more of the LBPs is able to bind to a greater or lesser extent.

21. The kit according to claim 20, wherein the replicable genetic package (RGP) is a filamentous bacteriophage.

22. The kit according to claim 21, wherein the filamentous bacteriophage is selected from the group consisting of fd, M13, f1, If1, 1ke, Zj/Z, Ff, Xf, Pf1, and Pf3.

23. The kit according to claim 20 or 21, wherein the cloning site replaces part of a gene encoding a surface protein which is required by the replicable genetic package (RGP) for binding to, and infection of, a host cell.

24. The kit according to claim 23, wherein the surface protein gene is gene III of the filamentous bacteriophages.

25. The kit according to claim 24, wherein the N-terminal 169 amino acids of gene III are replaced by the cloning site.

26. The kit according to claim 20, wherein the covalent attachment is facilitated by reacting the polypeptide with a cross-linking reagent.

27. The kit according to claim 26, wherein the cross-linking reagent is selected from the group consisting of N-succinimidyl 3-(2-pyridyldithio)propionate (SPDP), succinimidyl 4-(N-maleimidomethyl) cyclohexane-1-carboxylate (SMCC), m-maleimidobenzoyl-N-hydrosuccinimide ester (MBS), N-succinimidyl (4-iodacetyl) aminobenzoate (SIAB), and 1-ethyl-3-(3-dimethylaminopropyl) carbodiimide (EDC).

* * * * *

UNITED STATES PATENT AND TRADEMARK OFFICE
CERTIFICATE OF CORRECTION

PATENT NO.   : 5,514,548
DATED        : May 7, 1996
INVENTOR(S)  : Krebber et al.

It is certified that error appears in the above-identified patent and that said Letters Patent is hereby corrected as shown below:

Title page,
Item [75], delete "Klaus" and substitute therefor -- Claus --.

Column 1,
Line 1, insert -- A -- before "METHOD".

Column 3,
Line 30, delete "bactenophage" and substitute therefor -- bacteriophage --.
Line 44, delete "add" and substitute therefor -- acid --.
Line 56, delete "HI" and substitute therefor -- III --.

Column 4,
Line 18, delete "LMC" and substitute therefor -- IMC --.
Line 52, delete "F-pill" and substitute therefor -- F-pili --.

Column 5,
Line 11, delete "gene I11" and substitute therefor -- gene III --.
Line 14, delete "gene I11" and substitute therefor -- gene III --.
Line 40, delete "routS" and substitute therefor -- mutS --. Delete Mutt strains" and substitute therefor -- mutT strains --.
Line 46, delete "hydrazme" and substitute therefor -- hydrazine --.

Column 6,
Line 16, delete "LMC" and substitute therefor -- IMC --.
Line 16, insert -- a -- after "refers to".
Line 48, delete "class LI" and substitute therefor -- class II --.
Line 54, delete "adds" and substitute therefor -- acids --.
Line 64, delete "interact/on" and substitute therefor -- interaction --.
Line 67, after "invention" insert a colon -- : --.

Column 7,
Line 30, delete "done" and insert -- clone --.
Line 31, delete "adds" and insert -- acids --.
Line 46, delete "coil" and insert -- coli --.
Line 52, delete "CCC" and substitute therefor -- CCCC --.
Line 60, delete "oligonudeotide" and substitute therefor -- oligonucleotide --.
Line 66, delete "and no" and substitute therefor -- amino --.

UNITED STATES PATENT AND TRADEMARK OFFICE
CERTIFICATE OF CORRECTION

PATENT NO. : 5,514,548
DATED : May 7, 1996
INVENTOR(S) : Krebber et al.

It is certified that error appears in the above-identified patent and that said Letters Patent is hereby corrected as shown below:

Column 8,
Line 1, delete "ammo adds" and substitute therefor -- amino acids --.
Line 2, delete "adds" and substitute therfor -- acids --.
Line 4, delete "ammo" and substitute therefor -- amino --.
Line 5, delete "coil" and substitute therefor -- coli --.
Line 6, delete "ammo adds" and substitute therefor -- amino acids --.
Line 7, delete "coil" and substitute therefor -- coli --.
Line 38, delete "coil" and insert -- coli --.
Line 66, delete "sit" and insert -- site --.
Line 67, delete "sit" and insert -- site --.

Column 9,
Line 13, delete "TEA" and substitute therefor -- TTA --. Delete "GTC" and substitute therefor -- GTG --.
Line 14, delete "CCA" and substitute therefor -- GGA --. Delete "CCC" and substitute therefor -- GCC --.
Line 18, delete "LPM" and substitute therefor -- IPM --.
Line 64, delete "co,meeting" and substitute therefor -- connecting --.

Column 10,
Line 8, delete "µ-Subunit" and substitute therefor -- β-Subunit --.
Line 15, delete "NO:7)" and substitute therefor -- NO:13 --.
Line 31, delete "gone" and substitute therefor -- gene --.
Line 32, delete "pACYCI77" and substitute therefor -- pACYC177 --.
Line 47, delete "phase" and substitute therefor -- phage --.
Line 56, delete "Anti-Benzoylampidllin" and substitute therefor -- Anti-Benzoylampicillin --.
Line 58, delete "Encodine" and substitute therefor -- Encoding --.
Line 65, delete the first occurrence of "CCC" and substitute therefor -- CCG --.
Line 67, delete "(SEQ ID NO:2)" and substitute therefor -- (SEQ ID NO:23) --.

Column 11,
Line 3, delete "elycine" and substitute therefor -- glycine --. Delete "or" and substitute therefor -- of --.
Line 5, delete "pCK-IFMC" and substitute therefor -- pCK-IPMC --.
Line 47, delete "XLI-blueL and substitute therefor -- XL1-blue --.
Line 52, delete "refection" and substitute therefor -- infection --.

Column 12,
Line 9, delete "275" and substitute therefor -- 1275 --.
Line 36, delete "(2982)" and substitute therefor -- (1982) --.

UNITED STATES PATENT AND TRADEMARK OFFICE
CERTIFICATE OF CORRECTION

PATENT NO. : 5,514,548
DATED : May 7, 1996
INVENTOR(S) : Krebber et al.

It is certified that error appears in the above-identified patent and that said Letters Patent is hereby corrected as shown below:

Column 13,
Line 3, delete "(iii) NUMBER SEQUENCES:23" and substitute therefor

-- (i) APPLICANTS:     Claus Krebber, Simon Moroney, Andreas Plückthun and Christian Schneider (ii) TITLE OF INVENTION: A METHOD FOR IN VIVO SELECTION OF LIGAND-BINDING PROTEINS (iii) NUMBER OF SEQUENCES: 23

(iv) CORRESPONDENCE ADDRESS:
    (A) ADDRESSEE: James F. Haley, Jr., Esq. c/o FISH & NEAVE
    (B) STREET: 1251 Avenue of the Americas
    (C) CITY: New York
    (D) STATE: New York
    (E) COUNTRY: United States of America
    (F) ZIP: 10020

(v) COMPUTER READABLE-FORM:
    (A) MEDIUM TYPE: Floppy disk
    (B) COMPUTER: IBM PC compatible
    (C) OPERATING SYSTEM: PC-DOS/MS-DOS
    (D) SOFTWARE: PatentIn Release #1.0, Version #1.25 (EPO)

(vi) PRIOR APPLICATION DATA:
    (A) APPLICATION NUMBER: EP 93 10 2484.8
    (B) FILING DATE: 17-FEB-1993 --

UNITED STATES PATENT AND TRADEMARK OFFICE
CERTIFICATE OF CORRECTION

PATENT NO. : 5,514,548
DATED : May 7, 1996
INVENTOR(S) : Krebber et al.

It is certified that error appears in the above-identified patent and that said Letters Patent is hereby corrected as shown below:

Column 25,
Line 46, delete "mutt strains" and substitute therefor -- mutT strains --.

Signed and Sealed this

Fifteenth Day of January, 2002

Attest:

Attesting Officer

JAMES E. ROGAN
Director of the United States Patent and Trademark Office

SEQUENCE LISTING ( 1 ) GENERAL INFORMATION:

( i i i ) NUMBER OF SEQUENCES: 23

( 2 ) INFORMATION FOR SEQ ID NO: 1:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 1:

AATCATGAAA AAATTATTAT TCGCAA 26

( 2 ) INFORMATION FOR SEQ ID NO: 2:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 2:

AAAAGCTTAG TGATGGTGAT GGTGATGTCC GGAACCGGAG CC 42

( 2 ) INFORMATION FOR SEQ ID NO: 3:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 3:

AATCATGAAA AAATTATTAT TCGCAA 26

( 2 ) INFORMATION FOR SEQ ID NO: 4:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 4:

AAAAGCTTAT CCGGACGGAG CATTGACAGG AGGTTG                                    36

( 2 ) INFORMATION FOR SEQ ID NO: 5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 5:

AATCATGACC GATGATGAAG CCC                                                  23

( 2 ) INFORMATION FOR SEQ ID NO: 6:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 6:

AAAAGCTTAG TGATGGTGAT GGTGATGGAT TTCCCCTCGT GCTTT                          45

( 2 ) INFORMATION FOR SEQ ID NO: 7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 7:

AATCATGACA ACATTACTTA ACCCC                                                25

( 2 ) INFORMATION FOR SEQ ID NO: 8:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 8:

AAAAGCTTAG TGATGGTGAT GGTGATGGAT TTCCCCTCGT GCTTT                          45

( 2 ) INFORMATION FOR SEQ ID NO: 9:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 9:

CCGGACCGGG    10

( 2 ) INFORMATION FOR SEQ ID NO: 10:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 10:

CATGCCCGGT    10

( 2 ) INFORMATION FOR SEQ ID NO: 11:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 11:

CTAGATAAGG AAAAATCATG ATTTTTCCTT AT    32

( 2 ) INFORMATION FOR SEQ ID NO: 12:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 12:

AAAAGCTTAG TGATGGTGAT GGTGATGTCC GGACGGAGCA TTGACAGGAG GTTG    54

( 2 ) INFORMATION FOR SEQ ID NO: 13:

( i ) SEQUENCE CHARACTERISTICS:
        ( A ) LENGTH: 33 base pairs (B) TYPE: nucleic acid
(C) STRANDEDNESS: single
(D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 13:

GAGGACTAAA GACTTACGCA TGAGGAAGTT TCC    33

(2) INFORMATION FOR SEQ ID NO: 14:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 14:

TTGACAGGAG GTTGAGGGAA TTCCAGGTCA GACGATT    37

(2) INFORMATION FOR SEQ ID NO: 15:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 15:

CGAATAATAA TTTTTTCATG ATGAAAATCT CCAAAAAAAA    40

(2) INFORMATION FOR SEQ ID NO: 16:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 16:

TTTAATTGTA TCGGTCTCGA GAGGCCTTTA TCAGCTTGC    39

(2) INFORMATION FOR SEQ ID NO: 17:

(i) SEQUENCE CHARACTERISTICS:
(A) LENGTH: 38 base pairs
(B) TYPE: nucleic acid
(C) STRANDEDNESS: single
(D) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 17:

GCGGGCCGCA GGCCTCGAGA AATTCACCTC GAAAGCAA    38

( 2 ) INFORMATION FOR SEQ ID NO: 18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 18:

AGGCCTTAGA AAAACTCATC GAGC    24

( 2 ) INFORMATION FOR SEQ ID NO: 19:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 19:

AGGCCTGTTA CATTGCACAA GATAAAAATA TATCATAATG AACAATAAAA CTGTCT    56

( 2 ) INFORMATION FOR SEQ ID NO: 20:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 20:

AAATCATGAA AAAGACAGCT ATCGCG    26

( 2 ) INFORMATION FOR SEQ ID NO: 21:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO (i i i) ANTI-SENSE: NO (x i) SEQUENCE DESCRIPTION: SEQ ID NO: 21:

GGTCACGCTG CGCGTAACC                                                                 19

(2) INFORMATION FOR SEQ ID NO: 22:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i i i) ANTI-SENSE: NO (x i) SEQUENCE DESCRIPTION: SEQ ID NO: 22:

CCGGATGCCC CCATCACCAT CACCATCACT AATATTA                                            37

(2) INFORMATION FOR SEQ ID NO: 23:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i i i) ANTI-SENSE: NO (x i) SEQUENCE DESCRIPTION: SEQ ID NO: 23:

AGCTTAATAT TAGTGATGGT GATGGTGATG GGGGCAT                                            37